(12) United States Patent
Humble et al.

(10) Patent No.: US 7,160,246 B2
(45) Date of Patent: Jan. 9, 2007

(54) SYSTEM AND METHOD FOR REMOVING A PROTECTIVE COVER FROM A MEDICAL INSTRUMENT

(75) Inventors: Robin Charles Humble, Westlands (GB); Alexander S. Withers, Athens, TX (US); Kathy W. Zachry, Kingston, TN (US); Mark S. Dillon, Columbus, MS (US); Michael A. Gil, West Point, MS (US)

(73) Assignee: Microtek Medical, Inc., Columbus, MS (US)

( * ) Notice: Subject to any disclaimer, the term of this patent is extended or adjusted under 35 U.S.C. 154(b) by 375 days.

(21) Appl. No.: 10/688,675

(22) Filed: Oct. 17, 2003

(65) Prior Publication Data

US 2004/0127891 A1    Jul. 1, 2004

Related U.S. Application Data

(60) Provisional application No. 60/419,460, filed on Oct. 17, 2002.

(51) Int. Cl.
*A61B 1/00* (2006.01)

(52) U.S. Cl. ........................... 600/124; 600/121

(58) Field of Classification Search ............ 600/186, 600/121–124
See application file for complete search history.

(56) References Cited

U.S. PATENT DOCUMENTS

| | | | |
|---|---|---|---|
| 2,797,684 A | 7/1957 | Moore | 128/9 |
| 4,886,049 A | 12/1989 | Darras | 128/4 |
| 5,061,246 A | 10/1991 | Anapliotis | 604/171 |
| 5,217,001 A | 6/1993 | Nakao et al. | 128/4 |
| 5,466,898 A | 11/1995 | Gilbert et al. | 181/131 |
| 5,910,113 A | 6/1999 | Pruter | 600/437 |
| 2002/0082477 A1 | 6/2002 | Kim | 600/186 |

FOREIGN PATENT DOCUMENTS

EP    0 788 777 A1    8/1997

*Primary Examiner*—Rosiland Rollins
(74) *Attorney, Agent, or Firm*—Baker Botts L.L.P.

(57) ABSTRACT

According to one embodiment of the invention, a system for removing a cover from a medical instrument includes a flexible cover configured to cover at least a portion of a medical instrument, an insertion element coupled proximate a first end of the flexible cover, a pair of substantially parallel perforations formed in the insertion element, a pair of substantially parallel score lines formed in the cover and aligned with the pair of substantially parallel perforations. A portion of the insertion element between the pair of substantially parallel perforations is removable from the insertion element and a portion of the flexible cover between the pair of substantially parallel score lines is removable from the flexible cover when a force is applied to the portion of the insertion element between the pair of substantially parallel perforations.

37 Claims, 3 Drawing Sheets

SYSTEM AND METHOD FOR REMOVING A PROTECTIVE COVER FROM A MEDICAL INSTRUMENT

RELATED APPLICATIONS

This application claims the benefit of Ser. No. 60/419,460 titled "SYSTEM AND METHOD FOR REMOVING A PLASTIC COVER FROM A MEDICAL INSTRUMENT," filed provisionally on Oct. 17, 2002.

TECHNICAL FIELD OF THE INVENTION

The present invention relates generally to the medical field and, more particularly, to a system and method for removing a protective cover from a medical instrument.

BACKGROUND OF THE INVENTION

Medical equipment, particularly surgical equipment, oftentimes requires protective covers so that the equipment may be introduced into sterile fields and/or environments without jeopardizing the sterility of the fields and/or environments. Many of these sterile protective covers are conformed to the general shape of the equipment they cover and are single use disposable.

The process of removing these protective covers after the medical/surgical procedures have been completed is rather cumbersome and difficult due to the large size and volume of excess material that is present. Oftentimes, the equipment itself can become damaged due to the complexities of removing these plastic covers. Furthermore, the process of removing protective covers by methods of unfolding and uncovering are time-consuming in an environment that is highly sensitive to the time constraints of turning over the surgical suites between procedures.

SUMMARY OF THE INVENTION

According to one embodiment of the invention, a system for removing a cover from a medical instrument includes a flexible cover configured to cover at least a portion of a medical instrument, an insertion element coupled proximate a first end of the flexible cover, a pair of substantially parallel perforations formed in the insertion element, a pair of substantially parallel score lines formed in the cover and aligned with the pair of substantially parallel perforations. A portion of the insertion element between the pair of substantially parallel perforations is removable from the insertion element and a portion of the flexible cover between the pair of substantially parallel score lines is removable from the flexible cover when a force is applied to the portion of the insertion element between the pair of substantially parallel perforations.

Embodiments of the invention provide a number of technical advantages. Embodiments of the invention may include all, some, or none of these advantages. In one embodiment, the time required to remove a protective cover from medical equipment is reduced. In addition, possible damage to the medical equipment during cover removal due to equipment being dropped is eliminated. Possible exposure of staff to contaminated drape materials when removing from the medical equipment is substantially reduced. In the event of sterile barrier contamination, change-over time when re-draping is required is substantially reduced.

Other technical advantages are readily apparent to one skilled in the art from the following figures, descriptions, and claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EXAMPLE EMBODIMENTS OF THE INVENTION

Figure 1:
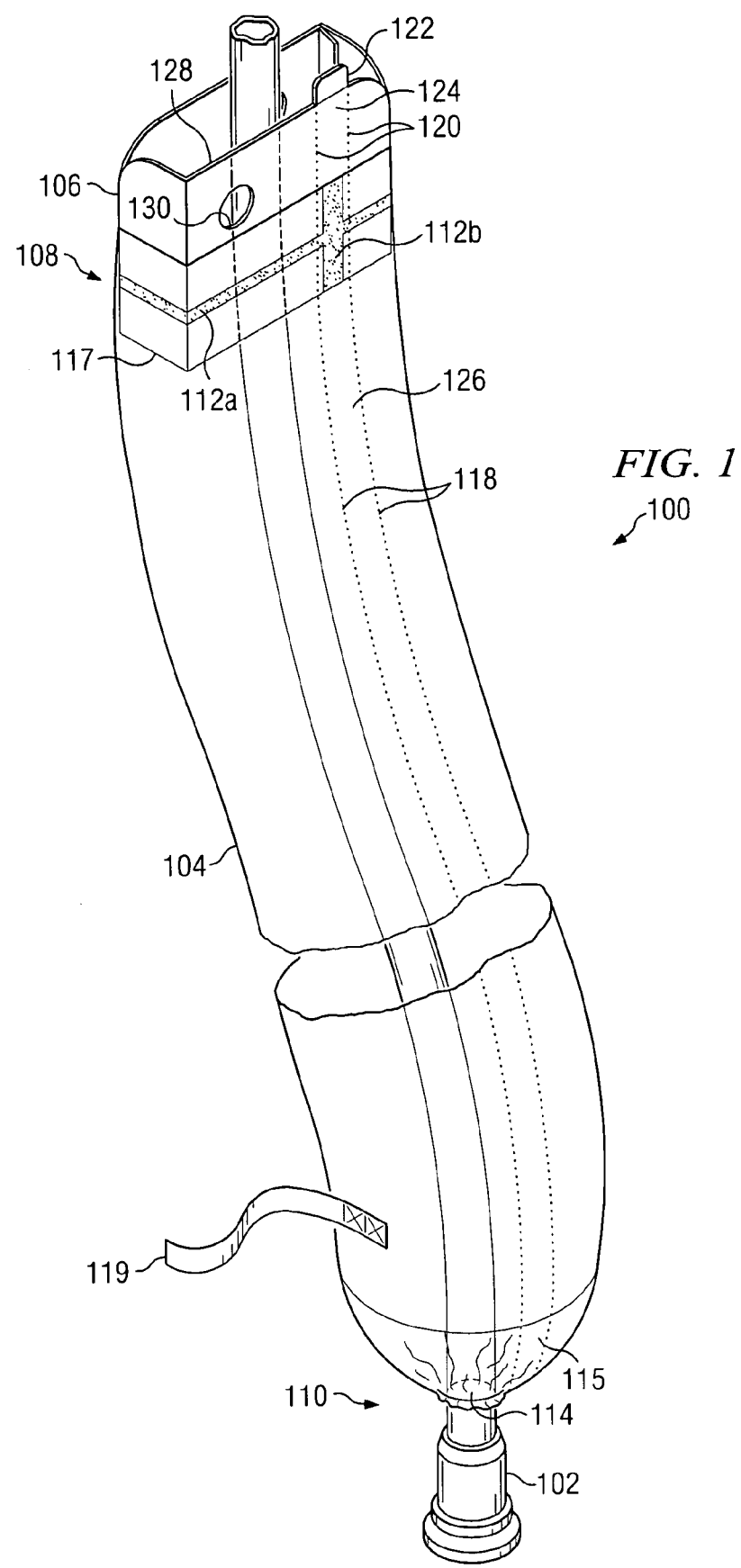
FIG. 1 is a perspective view of a system for protecting a medical instrument according to one embodiment of the invention.
Figure 2A:
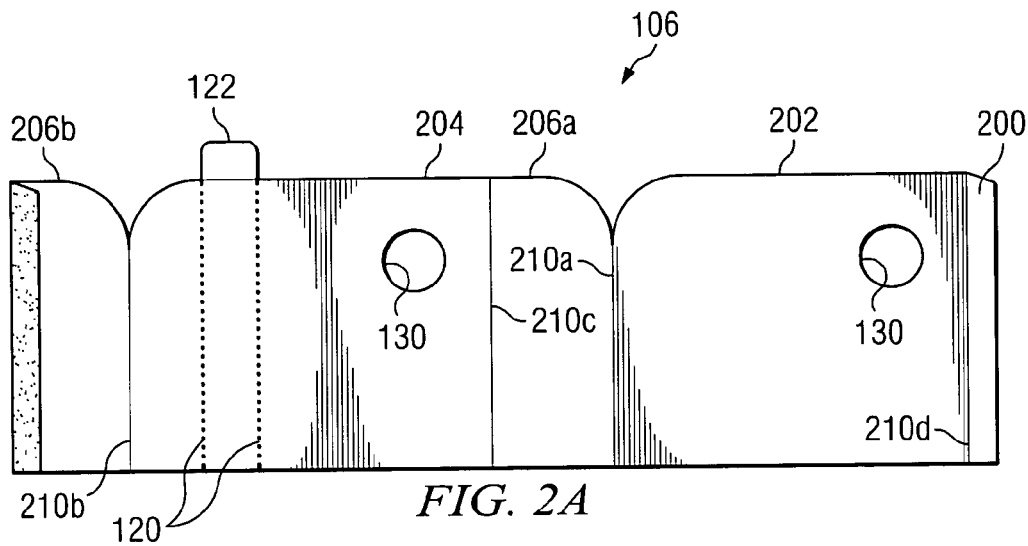
FIGS. 2A through 2C illustrate various views of an insertion element for use in the system of FIG. 1 according to one embodiment of the invention.
Figure 2B:
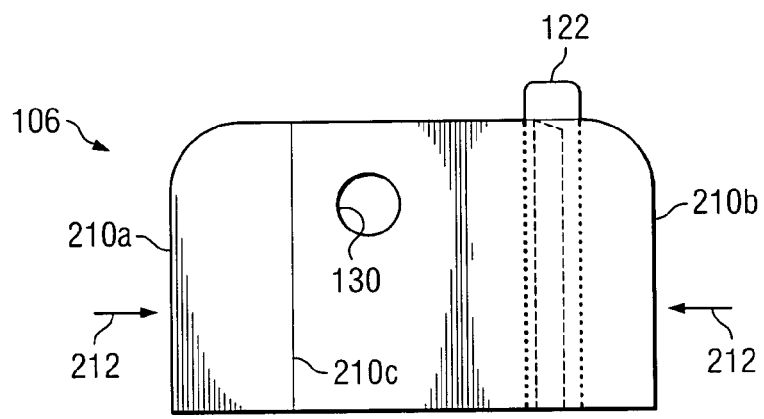
Figure 2C:
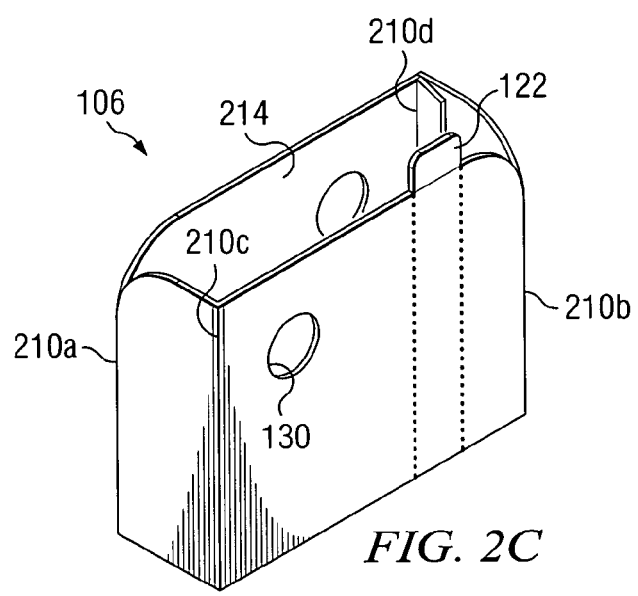
Figure 3:
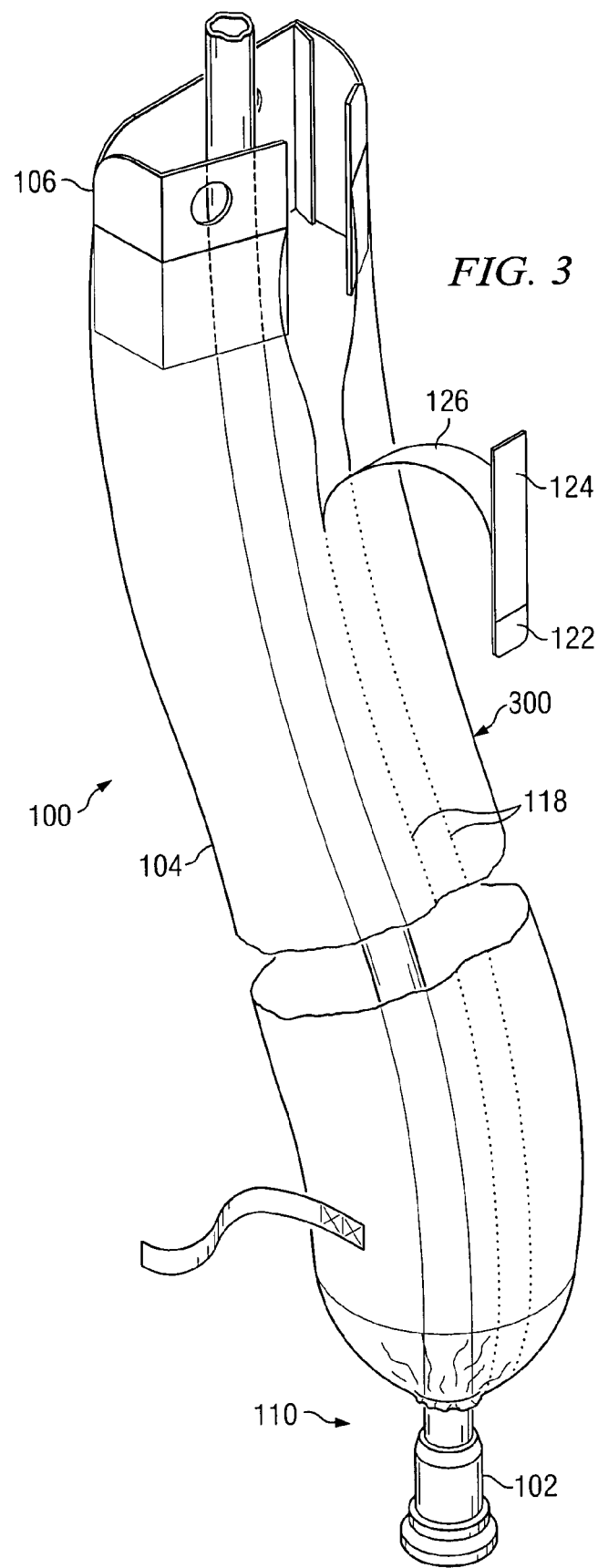
FIG. 3 is a perspective view of the system of FIG. 1 illustrating the removal procedure for the protective covering system according to one embodiment of the invention.

Example embodiments of the present invention and their advantages are best understood by referring now to FIGS. 1 through 3 of the drawings.

FIG. 1 is a perspective view of the system 100 for protecting a medical instrument 102 according to one embodiment of the invention. Although medical instrument 102 is illustrated in FIG. 1 as being an endoscope, any suitable medical or surgical instrument, such as a video camera, ultrasonic probe, and gamma probe, or other device desired to be protected from its environment by system 100 is contemplated by the present invention. In the illustrated embodiment, system 100 includes a flexible cover 104 configured to cover at least a portion of medical instrument 102 and an insertion element 106 coupled proximate a first end 108 of flexible cover 104.

Flexible cover 104 functions to protect at least a portion of medical instrument 102 so that medical instrument 102 may be introduced into sterile fields and/or environments without jeopardizing the sterility of the fields and/or environments. Flexible cover 104 may be formed from any suitable material; however, in one embodiment, flexible cover 104 is formed from a suitable polymer. Preferably, protective cover 104 conforms to the general shape of that portion of medical instrument 102 that it is covering. For example, in the illustrated embodiment, flexible cover is in the form of a generally tubular configuration so that it conforms to the general shape of medical instrument 102. However, flexible cover 104 may have any suitable shape and size.

Flexible cover 104 extends from first end 108 to a second end 110 proximate an end of medical instrument 102. Second end 110 may include, in some embodiments, an elastic end 115 that functions to provide some puncture resistance to second end 110 of flexible cover 104 to avoid any puncturing or tearing of flexible cover 104 when medical instrument 102 is inserted therethrough. Second end 110 may also include a tie-down strip 119 for securing second end 110 to medical instrument 102 to reduce the potential of interference from flexible cover 104 during a medical procedure. Tie-down strip 119 may be any suitable securing element, such as adhesive tape or a hook-and-loop type fastener, and may be coupled to second end 110 in any suitable manner.

Depending on the type of medical instrument 102 being protected by flexible cover 104, second end 110 may include an aperture 114 for disposing medical instrument 102 therethrough or, in some embodiments, may include a suitable perforated or scored section that facilitates the formation of an aperture when a force is applied to the perforated or scored section, such as when medical instrument 102 is inserted therethrough. In another embodiment, second end 110 is closed from its environment and has no openings formed therein. For example, if medical instrument 102 is an ultrasound probe, then second end 110 may be closed so that the ultrasound probe does not come into contact with a patient's body.

As described above, first end 108 couples to insertion element 106. In the illustrated embodiment, first end 108 is coupled to insertion element 106 with a suitable adhesive, as indicated by circumferential adhesive area 112a and longitudinal adhesive area 112b. Other suitable coupling methods are contemplated by the present invention for coupling first end 108 to insertion element 106. In addition, first end 108 may be coupled to an outside surface of insertion element 106 or an inside surface of insertion element 106 in any suitable location. In another embodiment, first end 108 is coupled to an end 117 of insertion element 106.

According to the teachings of one embodiment of the invention, flexible cover 104 includes a pair of score lines 118 formed therein. As illustrated below in conjunction with FIG. 3, score lines 118 facilitate the removal of flexible cover 104 from medical instrument 102. Although perforations may be used in lieu of score lines 118, it is preferable that score lines 118 be utilized because score lines 118 do not extend through the full thickness of flexible cover 104, whereas perforations would extend through the full thickness of flexible cover 104 and expose that portion of medical instrument 102 within flexible cover 104 to its environment. In the illustrated embodiment, score lines 118 extend from first end 108 to second end 110; however, score lines 118 may extend along any suitable length of flexible cover 104. There may also exist some embodiments in which score lines 118 do not exist in flexible cover 104. In the illustrated embodiment, score lines 118 are substantially parallel score lines and are separated by a distance of approximately one-half inch to approximately one and one-half inches, although other suitable distances may also be utilized depending on the type of material and configuration of flexible cover 104. In addition, score lines 118 do not have to be parallel, but may have any suitable relation to one another.

Insertion element 106, which is described in greater detail below in conjunction with FIGS. 2A through 2C, functions to facilitate the easy insertion of medical instrument 102 into flexible cover 104. Similar to flexible cover 104, insertion element 106 may have any suitable size and shape and may be formed from any suitable material. In the illustrated embodiment, insertion element 106 is of a generally rectangular shape and is formed from a cardboard material in order to provide some level of stiffness so that a user may easily insert medical instrument 102 therethrough.

According to the teachings of another embodiment of the invention, insertion element 106 includes a pair of perforations 120 formed therein and a pull tab 122 coupled to insertion element 106 proximate perforations 120. Although score lines may also be used in place of perforations 120, it is preferable that perforations 120 be utilized for ease of removal of a portion 124 disposed between perforations 120 during the removal of insertion element 106 from medical instrument 102. Similar to score lines 118 in flexible cover 104, perforations 120 are substantially parallel to one another and are separated by a distance of approximately approximately one-half inch to approximately one and one-half inches, although other suitable distances may also be utilized. In addition, it is preferably that perforations 120 generally align with score lines 118 in flexible cover 104 to facilitate the removal of portion 124 of insertion element 106 and a portion 126 disposed between score lines 118 in flexible cover 104 with one pulling motion on pull tab 122. This is described in greater detail below in conjunction with FIG. 3. Although pull tab 122 may be coupled to insertion element 106 in any suitable location, it is advantageous to couple pull tab 122 to a top edge 128 of insertion element 106 in a location where perforations 120 start.

Insertion element 106 may also include one or more gripping apertures 130 to allow a user to insert his or her fingers therein to manipulate insertion element 106 from a closed position to an open position, as described in more detail below in conjunction with FIGS. 2A through 2C. Gripping apertures 130 may be any suitable size and shape.

FIGS. 2A through 2C illustrate various views of insertion element 106 in accordance with one embodiment of the invention. Other suitable insertion elements may be utilized for system 100, such as lining members illustrated in U.S. Pat. No. 5,061,246, issued to Anapliotis, which is herein incorporated by reference. In the embodiment illustrated in FIGS. 2A through 2C, insertion element 106 is assumed to be formed from a single piece of cardboard material, although insertion element may be formed from multiple pieces and coupled together in any suitable manner.

Referring to FIG. 2A, insertion element 106 is illustrated in two-dimensional form after being stamped out of one piece of cardboard material. The layout of insertion element 106 in FIG. 2A includes a flap 200, a back 202, a front 204, and a pair of sidewalls 206a and 206b. Side wall 206b includes an adhesive area 208 that corresponds to the general shape of flap 200 so that adhesive area 208 and flap 200 may be coupled together, as described below in conjunction with FIG. 2B and 2C. Front 204 includes pull tab 122 which may be formed integral with insertion element 106 or may be a separate piece coupled to insertion element 106 in any suitable manner. Also illustrated are perforations 120 formed in front 204, and gripping apertures 130. Insertion element 106 also includes a plurality of fold lines 210a–d that define the corners of insertion element 106 when in an "open position," as illustrated in FIG. 2C.

Referring to FIG. 2B, insertion element 106 is formed into a "closed position" by folding front 204 over back 202 along fold line 210a and then folding side wall 206b along fold line 210b to adhesively couple adhesive area 208 to flap 200. This closed position for insertion element 106 facilitates the easy packing and shipping of system 100. This also facilitates the alignment of gripping apertures 130, as illustrated in FIG. 2B, which allows the user to insert a finger into gripping apertures 130 in order to unravel flexible cover 104 after removing from its shipping package. In addition to insertion element 106 being shipped in the flat, closed position, it is also desirable for flexible cover 104 to be shipped in a similar state. For example, as described in U.S. Pat. No. 5,061,246, flexible cover 104 may be shipped in a telescopic arrangement or may be shipped in a suitably folded rolled manner. In order to facilitate the insertion of medical instrument 102 within flexible cover 104, insertion element 106 needs to be transformed from the closed position in FIG. 2B to the open position in FIG. 2C. To accomplish this, a user merely has to apply pressure to the ends of insertion element 106 (which corresponds to fold lines 210a, 210b) as indicated by arrows 212. This then produces the open position configuration illustrated in FIG. 2C.

Referring to FIG. 2C, insertion element 106 is illustrated in its open position in which medical instrument 102 may now be inserted into and through insertion element 106 and into flexible cover 104 (not illustrated in FIG. 2C). The open position of insertion element 106 is illustrated in FIG. 2C facilitates the easy insertion of medical instrument 102 by providing a mouth 214 created by applying pressure to the ends of insertion element 106 as indicated by arrows 212 (FIG. 2B).

FIG. 3 is a perspective view of system 100 illustrating the removal procedure for insertion element 106 and flexible cover 104 according to one embodiment of the invention. Because the process of removing protective covers from medical and/or surgical instruments may be rather cumbersome and difficult due to the large size and volume of excess material that is present, it is desirable for system 100 to reduce the time and effort required to remove insertion element 106 and flexible cover 104 from medical instrument 102. This reduces possible damage to medical instrument 102 during the removal procedure and substantially reduces possible exposure of medical personnel to contaminated drape materials. System 100 accomplishes this by allowing a user to simply use his or her fingers or some other suitable instrument (not explicitly illustrated) to apply a pulling force to pull tab 122, which then removes portion 124 from insertion element 106 and portion 126 from flexible cover 104 that are disposed between perforations 120 and score lines 118, respectively. Once portion 126 has been removed from flexible cover 104 down to second end 110, then flexible cover 104 may be removed from medical instrument 102 and disposed of quickly and cleanly. Depending on the type of medical instrument 102 being utilized, portion 126 may not have to be removed all the way down to second end 110 but may stop at an intermediate portion 300 of flexible cover 104 for the removal thereof.

Although embodiments of the invention and their advantages are described in detail, a person skilled in the art could make various alterations, additions, and omissions without departing from the spirit and scope of the present invention.

What is claimed is:

1. A system for removing a cover from a medical instrument, comprising:
   a flexible cover having a general tubular configuration for covering at least a portion of an elongated medical instrument;
   an insertion element coupled proximate a first end of the flexible cover, the insertion element being selectively expandable from a closed position to an open position to facilitate insertion of the elongated medical instrument;
   a pair of substantially parallel perforations formed in the insertion element and separated by a distance of approximately one-half inch to one and one-half inches;
   a pair of substantially parallel score lines formed in the cover and aligned with the pair of substantially parallel perforations, the pair of substantially parallel score lines extending from the first end to a second end of the flexible cover and separated by a distance of approximately one-half inch to one and one-half inches; and
   a tab coupled to the insertion element proximate the pair of substantially parallel perforations, whereby the tab is adapted to remove a portion of the insertion element between the pair of substantially parallel perforations and a portion of the flexible cover between the pair of substantially parallel score lines when a pulling force is applied to the tab.

2. The system of claim 1, wherein a second end of the flexible cover distal the first end is closed.

3. The system of claim 1, wherein a second end of the flexible cover distal the first end includes an aperture.

4. The system of claim 1, wherein a second end of the flexible cover distal the first end includes a scored or perforated portion adapted to produce an aperture in the second end when a force is applied to the scored or perforated portion.

5. The system of claim 1, wherein the insertion element is coupled within the first end of the flexible cover.

6. The system of claim 1, wherein the insertion element is coupled on the outside of the first end of the flexible cover.

7. The system of claim 1, wherein the medical instrument is selected from the group consisting of an endoscope, an ultrasound probe, a gamma probe, and a video camera.

8. A system for removing a cover from a medical instrument, comprising:
   a flexible cover configured to cover at least a portion of a medical instrument;
   an insertion element coupled proximate a first end of the flexible cover;
   a pair of substantially parallel perforations formed in the insertion element; and
   a pair of substantially parallel score lines formed in the cover and aligned with the pair of substantially parallel perforations, whereby a portion of the insertion element between the pair of substantially parallel perforations is removable from the insertion element and a portion of the flexible cover between the pair of substantially parallel score lines is removable from the flexible cover when a force is applied to the portion of the insertion element between the pair of substantially parallel perforations.

9. The system of claim 8, further comprising a tab coupled to the insertion element proximate the pair of substantially parallel perforations, whereby the tab is adapted to remove the portion of the insertion element between the pair of substantially parallel perforations and the portion of the cover between the pair of substantially parallel score lines when a pulling force is applied to the tab.

10. The system of claim 8, wherein the flexible cover is of a generally tubular configuration and is formed from a polymer.

11. The system of claim 8, wherein a second end of the flexible cover distal the first end is closed.

12. The system of claim 8, wherein a second end of the flexible cover distal the first end includes an aperture.

13. The system of claim 8, wherein a second end of the flexible cover distal the first end includes a scored or perforated portion adapted to produce an aperture in the second end when a force is applied to the scored or perforated portion.

14. The system of claim 8, wherein the insertion element is formed from cardboard.

15. The system of claim 8, wherein the insertion element is selectively expandable from a closed position to an open position.

16. The system of claim 8, further comprising a pair of gripping apertures formed in the insertion element.

17. The system of claim 8, wherein the insertion element is coupled within the first end of the flexible cover.

18. The system of claim 8, wherein the insertion element is coupled on the outside of the first end of the flexible cover.

19. The system of claim 8, wherein the pair of substantially parallel perforations and the pair of substantially parallel score lines are each separated by a distance of approximately one-half inch to one and one-half inches.

20. The system of claim 8, wherein the pair of substantially parallel score lines extend from the first end to a second end of the flexible cover.

21. The system of claim 8, wherein the pair of substantially parallel score lines extend from the first end to an intermediate portion of the flexible cover.

22. The system of claim 8, wherein the medical instrument is selected from the group consisting of an endoscope, an ultrasound probe, a gamma probe, and a video camera.

23. A method for removing a cover from a medical instrument, comprising:
    covering at least a portion of a medical instrument with a flexible cover, the flexible cover having an insertion element coupled proximate a first end of the flexible cover;
    removing a portion of the insertion element disposed between a pair of substantially parallel perforations formed in the insertion element by applying a force to the portion of the insertion element disposed between the pair of substantially parallel perforations; and
    removing an elongated portion of the flexible cover disposed between a pair of substantially parallel score lines formed in the flexible cover and aligned with the pair of substantially parallel perforations in the insertion element by continuing to apply the force to the portion of the insertion element disposed between the pair of substantially parallel perforations.

24. The method of claim 23, wherein the covering step comprises expanding the insertion element from a closed position to an open position, and inserting the portion of the medical instrument through the insertion element and into the flexible cover.

25. The method of claim 23, wherein the pair of substantially parallel perforations and the pair of substantially parallel score lines are each separated by a distance of approximately one-half inch to one and one-half inches.

26. The method of claim 23, wherein the pair of substantially parallel score lines extend from the first end to a second end of the flexible cover.

27. The method of claim 23, wherein the pair of substantially parallel score lines extend from the first end to an intermediate portion of the flexible cover.

28. The method of claim 23, wherein the medical instrument is selected from the group consisting of an endoscope, an ultrasound probe, a gamma probe, and a video camera.

29. A system for removing a cover from a medical instrument, comprising:
    a flexible cover configured to cover at least a portion of a medical instrument;
    an insertion element coupled proximate a first end of the flexible cover;
    a pair of substantially parallel perforations formed in the insertion element; and
    whereby a portion of the insertion element between the pair of substantially parallel perforations is removable from the insertion element and a portion of the flexible cover is removable from the flexible cover when a force is applied to the portion of the insertion element between the pair of substantially parallel perforations.

30. The system of claim 29, further comprising a tab coupled to the insertion element proximate the pair of substantially parallel perforations, whereby the tab is adapted to remove the portion of the insertion element between the pair of substantially parallel perforations and the portion of the cover when the force is applied to the tab.

31. The system of claim 29, wherein a second end of the flexible cover distal the first end is closed.

32. The system of claim 29, wherein a second end of the flexible cover distal the first end includes an aperture.

33. The system of claim 29, wherein a second end of the flexible cover distal the first end includes a scored or perforated portion adapted to produce an aperture in the second end when a force is applied to the scored or perforated portion.

34. The system of claim 29, wherein the insertion element is coupled within the first end of the flexible cover.

35. The system of claim 29, wherein the insertion element is coupled on the outside of the first end of the flexible cover.

36. The system of claim 29, wherein the pair of substantially parallel perforations are separated by a distance of approximately one-half inch to one and one-half inches.

37. The system of claim 29, wherein the medical instrument is selected from the group consisting of an endoscope, an ultrasound probe, a gamma probe, and a video camera.

\* \* \* \* \*